United States Patent [19]
Carrigan

[11] 3,970,083
[45] July 20, 1976

[54] ANKLE SUPPORT

[76] Inventor: Gordon R. Carrigan, Rte. 1, Box 608, West Linn, Oreg. 97068

[22] Filed: Sept. 11, 1974

[21] Appl. No.: 504,899

[52] U.S. Cl. .................................. 128/166; 36/89
[51] Int. Cl.[2] ........................................ A61F 13/06
[58] Field of Search ............ 128/166, 165, 155, 156, 128/157, 87; 36/2.5 N

[56] References Cited
UNITED STATES PATENTS

| | | | |
|---|---|---|---|
| 332,728 | 12/1885 | McEwen | 128/166 |
| 737,959 | 9/1903 | Posner | 128/166 |
| 1,084,197 | 1/1914 | Collis | 128/166 |
| 1,231,332 | 6/1917 | Collis | 128/166 |
| 1,658,037 | 2/1928 | Bromley | 128/166 |
| 3,073,305 | 1/1963 | Biggs, Jr. et al. | 128/166 |

*Primary Examiner*—John D. Yasko
*Attorney, Agent, or Firm*—Kolisch, Hartwell, Dickinson & Stuart

[57] ABSTRACT

An ankle support including a pliable single-piece jacket fittable about a person's foot and ankle. Joined to opposite sides of the jacket are elongated stiffening strips which define generally inverted-T-shaped stiffened regions in such sides. The support may be used on either a left or a right foot. A single seam which joins a pair of edges in the jacket is positioned, for wearing comfort reasons, to lie beneath a person's foot with the jacket fitted in place.

8 Claims, 5 Drawing Figures

ANKLE SUPPORT

BACKGROUND AND SUMMARY OF THE INVENTION

This invention pertains to an ankle support of the type that may be removably laced on and about a person's ankle and foot.

Ankle sprains are a common injury in many types of sports. The usual sprain results from inward turning of the foot which ruptures the connections between various lateral ligaments that connect the foot and leg bones at the ankle joint.

One of the most common current methods of protecting against such an injury, or of strenthening an ankle already weakened by such an injury, is so-called taping. Taping, properly done, is an art, is extremely time consuming, and can be very costly. The cost of taping is measured not only by the time spent by the person doing the taping, but also by the enormous amount of tape which is used, and after use discarded.

Attempts have been made to provide lace-on type ankle supports, but in virtually every instance such prior art devices, while perhaps somewhat minimizing the chance of sprain injury to an ankle, have unpleasantly and unnecessarily restricted ankle and foot movement.

A general object of the present invention is to provide a novel ankle support which both protects an ankle against sprain injury, and yet simultaneously permits substantially full freedom of movement of a foot.

According to a preferred embodiment of the invention, an ankle support is proposed which includes a pliable singlepiece jacket that is fittable about a person's foot and ankle. Joined to opposite sides of the jacket are elongated stiffening strips which define generally inverted-T-shaped stiffened regions in such sides. The support is laterally symmetrical, and may be used on either a left or a right foot. It is secured in place by lacing. A single seam, which joins a pair of edges in the jacket, is positioned, for wearing comfort reasons, to lie beneath a person's foot with the jacket fitted in place. The stiffening strips mentioned are so oriented that, with a jacket in place, these strips are aligned generally with key natural ligaments in an ankle, and particularly with natural ligaments on the lateral side of an ankle, whereby the strips reinforce these ligaments.

Importantly, the jacket and stiffening strips do not have a splinting effect at the ankle joint, and hence do not appreciably restrict normal foot movement.

Fitting and securing of a support is a matter which can be accomplished extremely quickly and by the wearer himself. Hence, the negative cost and time factors attending taping are avoided.

These and other objects and advantages which are attained by the invention will become more fully apparent as the description which follows is read in conjunction with the accompanying drawings.

Figure 5:
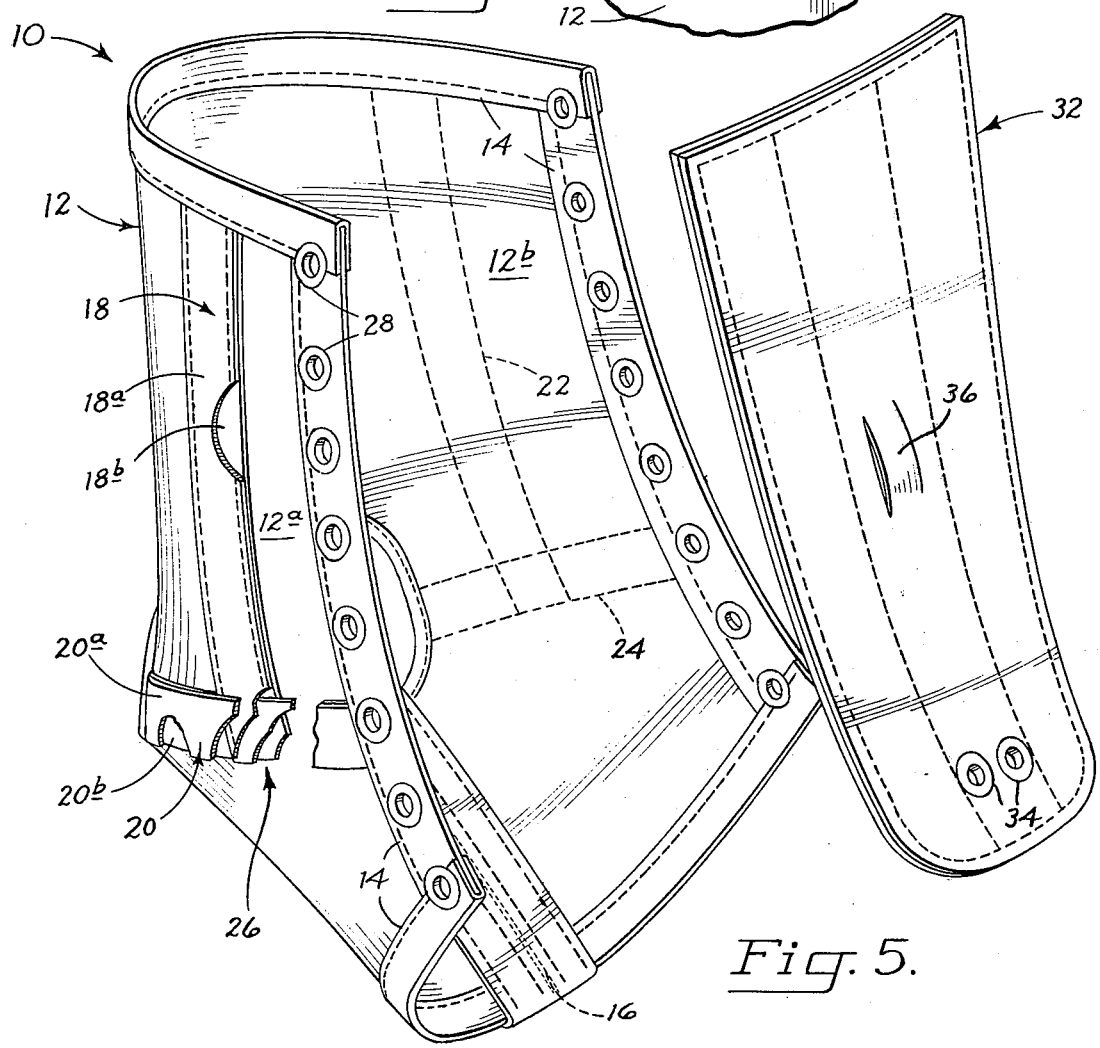

And, FIG. 5 is an exploded perspective view, with the support removed, further illustrating the construction of the support of the instant invention.

DETAILED DESCRIPTION OF THE INVENTION

Figure 1:
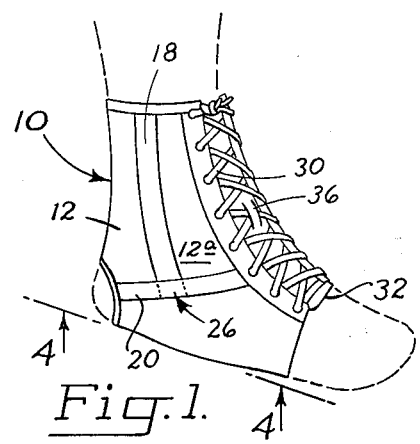
FIG. 1 is a side perspective view showing an ankle support, as contemplated herein, fitted in place on a person's right foot and ankle.
Figure 4:
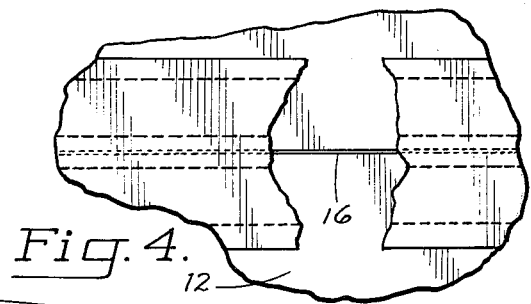
FIG. 4 is a bottom view taken generally along line 4—4 in FIG. 1.

Turning now to the drawings, and referring first to FIGS. 1, 4 and 5, indicated generally at 10 is an ankle support constructed in accordance with the present invention. Support 10, which is shown fitted in place on a person's right foot (over the sock), includes a jacket 12, formed of a single web of flexible material, such as a conventional nylon-vinyl material. The jacket is formed in a relatively well-known pattern whereby it will fit, as shown in FIGS. 1 and 4, snugly about a wearer's foot and ankle. Different sizes of jackets may, of course, be made to accommodate different wearers. The margins of the jacket are reinforced with a suitable binding, such as that shown at 14—this binding herein being formed of the same material used in the jacket.

According to the invention, but a single pair of edges in the jacket are joined to form a single seam therein, which seam is shown at 16 in FIG. 4, and is disposed to extend along the bottom of a wearer's foot with the jacket in place. The reason for this type of construction is to place the seam at a location where it will cause minimum irritation to a wearer.

Attached as by sewing to the outer surfaces of the opposite sides 12a, 12b in the jacket, are stacks of elongated stiffening strips, such as the two stacks shown at 18, 20 in FIG. 1 on side 12a in the jacket. A like set of stacks 22, 24 (see FIG. 5) is provided on the outer side of jacket side 12b.

As can be seen in FIGS. 1 and 5, the stacks of stiffening strips define generally inverted-T-shaped stiffened regions on the opposite sides of the jacket. As will be noted particularly in FIG. 5, where portions of stacks 18, 20 are broken away to illustrate details of construction, stack 18 includes a pair of overlapping strips 18a, 18b, and likewise, stack 20 includes a pair of overlapping strips 20a, 20b. Strips 18a, 18b, with the jacekt positioned as it would be worn on a person's foot, extend along a generally forwardly and downwardly inclined course, which curves forwardly adjacent the lower ends of the strips. Strips 20a, 20b in stack 20 extend along another course which is, generally speaking, an upwardly and forwardly inclined course. At the region indicated generally at 26 where the courses of the two stacks intersect, strips 18a, 18b, 20a, 20b overlap one another in a multiple layer sandwich construction, as can be seen in FIG. 5.

An overlapping strip construction like that just described with respect to stacks 18, 20 also characterizes the construction and intersection of stacks 22, 24.

The two strips in a stack herein are each formed of the same material used in the jacket.

Distributed along what are the confronting edges of jacket sides 12a, 12b (when the jacket is mounted in place) are a plurality of conventional lacing eyelets, such as the eyelets shown at 28. These eyelets are adapted to receive the usual tying and binding lace, such as lace 30.

Also included in support 10 is an elongated tongue 32 which is separate from jacket 12 (see particularly FIG. 5). At the base of the tongue are two eyelets 34, by means of which the tongue is captured through stringing of lace 30 through these eyelets. Above these two eyelets along the tongue, and on the top side of the tongue, is a strap 36 through which upper portions of the lace are inserted with fitting of the support in place. Tongue 32 is preferably a multiple layer construction including multiple layers of substantially the same material used in the jacket. Strap 36 is formed herein by a pair of slits cut in the top layer in the tongue.

It will be apparent from the above description, that support 10 has lateral symmetry—a feature making it, so to speak, a universal support which may be fitted on either a left or a right foot. According to the invention, the stiffened regions in the jacket, defined by the stacks of strips, are intended substantially to parallel key natural ligaments found in a person's foot at the ankle joint. Further, that portion of the jacket which is reinforced where the lower ends of the strips in stacks 18, 22 sandwich with midportions of the strips in stacks 20, 24 is intended, on the lateral side of a wearer's foot, to overlie that portion of the wearer's Fibula bone known as the Lateral Malleolus.

Figure 2:
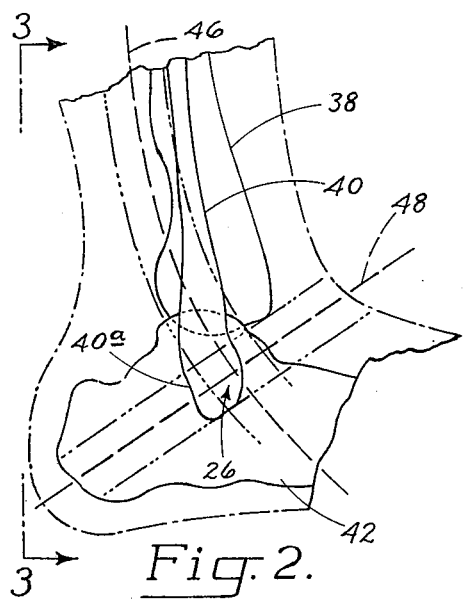
FIG. 2 is a simplified fragmentary schematic view, from about the same aspect as FIG. 1, showing the relationships of stiffened regions in the support to elements within the foot and ankle of FIG. 1.
Figure 3:
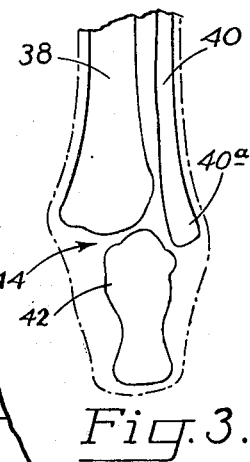
FIG. 3 is a view taken generally along the line 3—3 in FIG. 2.

Referring to FIGS. 2 and 3, shown in these figures is a very simplified schematic representation of the relationships of bones adjacent the ankle of a person's right foot. In particular, at 38 is shown the right Tibia, at 40 is shown the right Fibula, and at 42 is shown the right Talus. As can be seen, the lower ends of the Tibia and Fibula define a socket 44 for receiving an upwardly projecting portion of the rear end of the Talus.

It would needlessly complicate these two drawing figures to include sketches of the various ligaments in the region of adjacency between these three bones, but suffice it to say, what is well known to those familiar with anatomy, that a plurality of different ligaments extend between and interconnect these bones, to permit relative movement therebetween without dislocation of the bones. In very general terms, and for the purpose of description herein, these ligaments may be thought of as being divisible into two broad categories—namely, medial ligaments which are on the medial (inner) side of the foot, and which interconnect the Tibia and the Talus, and lateral ligaments which are on the lateral (outer) side of the foot, and which interconnect the Fibula and the Talus. The medical ligaments are extremely strong and require little reinforcement. The lateral ligaments, however, are quite weak, and it is their rupture, with inward turning of the Talus relative to the Tibia and Fibula, which produces the usual ankle sprain injury.

Referring particularly to FIG. 2, the lateral ligaments, while actually extending in many different specific directions, may be thought of as extending along two primary courses indicated generally by the dashed lines shown at 46, 48. Those ligaments which extend generally along course 46, it will be seen, extend in a generally downwardly and forwardly curved, inclined path. Those which extend along course 48 lie along a generally upwardly and forwardly inclined path.

With support 10 fitted and secured on the right foot as shown in FIG. 1, stacks 18, 20 on side 12a in the jacket extend generally as shown by the dash-triple-dot and dash-double-dot lines contained in FIG. 2. Thus, it will be noted that the strips in stack 18 generally follow and overlie course 46 (e.g., generally parallel this course), whereas the strips in stack 20 generally follow and overlie course 48. Further, it will be noted that where the strips in the stacks overlap at region 26, this region is disposed substantially directly over the lower extremity of the Fibula, which lower extremity is known as the Lateral Malleolus. This portion of the Fibula is designated 40a in FIGS. 2 and 3.

It has been found through extensive actual testing that use of a support such as that proposed herein appreciably reduces the likelihood of an ankle sprain injury. Significantly contributing to this performance is that the stiffened regions along the sides of the jacket in the support, with the jacket in place, and particularly along the lateral side of a foot, substantially parallel those predominant natural ligaments at the ankle joint which maintain the bones in the foot and leg in the proper relative positions. These stiffened regions sufficiently reinforce such ligaments that rupturing of the lateral ligaments is quite unlikely. The portion of overlap between the two stacks of stiffening strips, lying as it does (on the lateral side of the jacket) in place directly adjacent the Lateral Malleolus, has been found to contribute appreciably to the support's ability to minimize ankle injuries.

In addition to the natural ligament reinforcement which is afforded by the special positioning of stiffening strips herein, this positioning, following the courses of natural ligaments, permits substantially normal foot movement. In other words, the support of the invention does not have any appreciable splinting or motion-limiting effect on a foot. This, of course, is an important consideration.

It is thus believed apparent that a unique ankle support is proposed by the invention which means all of the objects, and offers all of the advantages, ascribed to it earlier. It is evident that a relatively simple construction is proposed, and that this construction can be adapted to fit ankles of many different sizes. Mounting of a support in place is something which requires no skill, and can be done quickly by the wearer. Universality in the support further simplifies the mounting procedure.

It will be evident to those skilled in the art that while a certain material which has been found to be practical has been used in the support described herein, other flexible materials may also be used.

Thus, while a preferred embodiment and certain modifications of the invention have been suggested and described herein, it will be apparent to those skilled in the art that other variations and modifications may be made without departing from the spirit of the invention.

It is claimed and desired to secure by Letters Patent:

1. An ankle support in operative condition comprising
a pliable jacket removably fitted about a person's foot and ankle, including a pair of side expanses which extend over opposite sides of the ankle,
a first elongated stiffening strip joined to the outside of and stiffening one elongated region in that expanse which extends over the lateral side of the ankle, said first stiffening strip extending over the Lateral Malleolus in the ankle, along a course substantially paralleling natural ligaments in the ankle, and
a second elongated stiffening strip joined to the outside of and stiffening another elongated region of the same expanse, said second stiffening strip having one end overlapping said first stiffening strip at a point therealong which is adjacent the Lateral Malleolus, and extending upwardly away from its said one end along a course substantially paralleling other natural ligaments in the ankle, said first and second stiffening strips being arranged in a generally T-shaped configuration on said expanse of said jacket.

2. An ankle support comprising a pliable jacket securably fittable about a person's foot and ankle, elongated stiffening means joined to the outside of said jacket along substantially its entire length on at least one side thereof forming a plurality of elongated stiffened regions in said one side, which regions extend along different courses that are at an angle to one another and intersect, with the stiffening means overlapping at the point of intersection of said courses, said regions being adapted, with said jacket fitted in place on an ankle, generally to parallel natural ligaments in the ankle, with said point of intersection of said courses extending over the Lateral Malleolus in the ankle.

3. The support of claim 2, wherein said stiffening means, for each stiffened region, comprises at least one elongated stiffening strip attached to said jacket at said region.

4. The support of claim 2, wherein said stiffening means, for each stiffened region, comprises plural elongated, stacked stiffening strips attached to said jacket at said region.

5. The support of claim 2, wherein said stiffening means, for each stiffened region, comprises plural, elongated, stacked stiffening strips attached to said jacket at said region, with all of said strips overlapping one another adjacent the point of intersection of said courses.

6. The support of claim 2, wherein said stiffened regions form a generally T-shaped configuration on said one side of said jacket.

7. An ankle support comprising a pliable jacket securably fittable about a person's foot and ankle, and two pairs of elongated stiffening strips joined to the outside of said jacket and disposed with one pair on one side of the jacket and the other pair on the opposite side of the jacket, the two strips in a pair of intersecting and overlapping one another to form a generally T-shaped stiffened region in the associated side of the jacket, with the region of overlapping of said strips being adapted, with said jacket fitted in place on an ankle, to extend over the Lateral Malleolus in the ankle.

8. The support of claim 7, wherein said jacket is formed of a single web of material including but a single seam between edges in said web, said seam being positioned to lie below the bottom of a person's foot with the jacket fitted in place.

* * * * *

UNITED STATES PATENT OFFICE
CERTIFICATE OF CORRECTION

PATENT NO. : 3,970,083
DATED : July 20, 1976
INVENTOR(S) : Gordon R. Carrigan

It is certified that error appears in the above-identified patent and that said Letters Patent are hereby corrected as shown below:

Column 2, line 44, change "jacekt" to --jacket--

Column 3, line 45, change "medical" to --medial--

Column 6, line 18, delete "of"

Signed and Sealed this

Sixteenth Day of November 1976

[SEAL]

Attest:

RUTH C. MASON
Attesting Officer

C. MARSHALL DANN
Commissioner of Patents and Trademarks